(12) United States Patent
Shreiber et al.

(10) Patent No.: US 9,275,437 B2
(45) Date of Patent: Mar. 1, 2016

(54) METHOD FOR EFFICIENT DIGITAL SUBTRACTION ANGIOGRAPHY

(71) Applicant: Algotec Systems Ltd., Rochester, NY (US)

(72) Inventors: Reuven R. Shreiber, Raanana (IL); Guy E. Engelhard, Raanana (IL)

(73) Assignee: Algotec Systems Ltd. (IL)

( * ) Notice: Subject to any disclaimer, the term of this patent is extended or adjusted under 35 U.S.C. 154(b) by 220 days.

(21) Appl. No.: 13/803,466

(22) Filed: Mar. 14, 2013

(65) Prior Publication Data

US 2014/0270437 A1 Sep. 18, 2014

(51) Int. Cl.
*G06K 9/00* (2006.01)
*G06T 5/00* (2006.01)
*G06T 5/50* (2006.01)
*G06T 7/00* (2006.01)
*A61B 6/00* (2006.01)

(52) U.S. Cl.
CPC .................. *G06T 5/002* (2013.01); *A61B 6/481* (2013.01); *A61B 6/486* (2013.01); *A61B 6/504* (2013.01); *G06T 5/50* (2013.01); *G06T 7/0024* (2013.01); *G06T 2207/20224* (2013.01); *G06T 2207/30101* (2013.01)

(58) Field of Classification Search
CPC ........ A61B 6/504; A61B 6/503; A61B 6/487; A61B 6/5217; A61B 6/463; A61B 6/486; A61B 6/5264; A61B 6/481; A61B 5/02007; A61B 5/113; A61B 5/4312; A61B 5/7425; A61B 5/055; A61B 10/0041; A61B 8/0883; A61B 8/0891; A61B 8/463; A61B 8/481; A61B 8/5276; G06K 2209/051; G06K 9/6206; G06K 9/6807

USPC .......................................................... 382/130
See application file for complete search history.

(56) References Cited

U.S. PATENT DOCUMENTS

| | | | | |
|---|---|---|---|---|
| 6,483,891 B1 * | 11/2002 | Lazarev | ............... | A61B 6/0435 378/37 |
| 2004/0189796 A1 * | 9/2004 | Ho | ........................ | H04N 13/026 348/51 |
| 2006/0067570 A1 * | 3/2006 | Onishi | .................... | G06T 7/001 382/147 |
| 2006/0133660 A1 * | 6/2006 | Ogi | ........................ | G06T 7/001 382/149 |
| 2006/0209095 A1 * | 9/2006 | Hsu | ....................... | G09G 3/3611 345/690 |
| 2006/0239585 A1 * | 10/2006 | Valadez | ................ | G06T 3/0075 382/275 |
| 2007/0036442 A1 * | 2/2007 | Stoffer | ................... | H04N 19/50 382/232 |
| 2007/0238951 A1 * | 10/2007 | Ferenczi | ................ | A61B 5/055 600/407 |
| 2009/0185730 A1 * | 7/2009 | Baumgart | ............ | A61B 6/4441 382/130 |
| 2010/0091194 A1 * | 4/2010 | Lei | ............................ | G06T 5/50 348/607 |
| 2010/0202687 A1 * | 8/2010 | Melbourne | ........... | G06T 7/0034 382/173 |

(Continued)

OTHER PUBLICATIONS

Frank R. Korosec, Richard Frayne, Thomas M. Grist, Charles A. Mistretta, "Time-Resolved Contrast-Enhanced 3D MR Angiography", Williams & Wilkins,1996.*

(Continued)

*Primary Examiner* — Stephen R Koziol
*Assistant Examiner* — Shaghayegh Azima

(57) ABSTRACT

A system and method for performing DSA (digital subtraction angiography), which does not require a non-enhanced or "mask" image to be obtained.

19 Claims, 4 Drawing Sheets

(56) References Cited

U.S. PATENT DOCUMENTS

| | | | |
|---|---|---|---|
| 2010/0235352 A1 | 9/2010 | Slutsky et al. | |
| 2010/0246975 A1* | 9/2010 | Tsukiori | G06K 9/00013 382/209 |
| 2011/0001884 A1* | 1/2011 | Iketani | G06T 7/2053 348/699 |
| 2011/0025857 A1* | 2/2011 | Seigneurbieux | H04N 19/156 348/192 |
| 2011/0081042 A1* | 4/2011 | Kim | H04N 13/0022 382/100 |
| 2011/0103671 A1* | 5/2011 | Meetz | G06T 7/0012 382/131 |
| 2012/0007895 A1* | 1/2012 | Kim | H04N 13/0025 345/690 |
| 2012/0105657 A1* | 5/2012 | Yokohata | H04N 5/2257 348/208.4 |
| 2012/0201439 A1* | 8/2012 | Rauch | G06T 7/20 382/130 |
| 2012/0232378 A1* | 9/2012 | Messroghli | G01R 33/4818 600/413 |
| 2012/0238870 A1* | 9/2012 | Smith | A61B 6/025 600/431 |
| 2012/0269384 A1* | 10/2012 | Jones | G06K 9/00201 382/103 |
| 2013/0070995 A1* | 3/2013 | Chou | G06T 7/0032 382/131 |
| 2013/0094734 A1* | 4/2013 | Rauch | G06T 7/0038 382/130 |
| 2013/0188040 A1* | 7/2013 | Kamen | G06F 19/3418 348/135 |
| 2014/0003690 A1* | 1/2014 | Razeto | G06T 7/003 382/131 |
| 2014/0267837 A1* | 9/2014 | Tsuji | H04N 5/32 348/241 |
| 2015/0016728 A1* | 1/2015 | Parthasarathy | G06T 7/0028 382/195 |

OTHER PUBLICATIONS

Scale-Space and Edge Detection Using Anisotropic Diffusion, Pietro Perona et al., IEEE Transactions on Pattern Analysis and Machine Intelligence, vol. 12, No. 7, Jul. 1990, pp. 629-639.

Algorithms for radiological image registration and their clinical application, D.J. Hawkes, J. Anat., 1998, 193, pp. 347-361.

Image registration: an essential tool for nuclear medicine, Hutton et al., European Journal of Nuclear Medicine, vol. 29, pp. 559-577, 2002.

* cited by examiner

METHOD FOR EFFICIENT DIGITAL SUBTRACTION ANGIOGRAPHY

FIELD OF THE INVENTION

The present invention relates to a system and method for an alternative method of performing efficient digital subtraction angiography and particularly, but not exclusively, to automatic efficient digital subtraction angiography in image data of bodily tissue and/or object feature analysis in image data from non-biological subjects.

BACKGROUND OF THE INVENTION

Angiography refers generally to the capture and representation of blood vessels or vasculature of the human body by means of X-ray imaging, i.e., X-ray vascular imaging. X-ray diagnostic imaging systems may be used for angiographic imaging procedures such as digital subtraction angiography (DSA), and live fluoroscopic roadmapping. As currently practiced in the art, digital subtraction angiography or DSA is an imaging method used for visualizing blood vessels inside a patient's body that includes injecting a contrast medium bolus that is substantially opaque to X-rays into the blood vessels or vasculature under study as images are acquired by the X-ray diagnostic imaging system. Prior to acquisition of the contrast image, a mask image without contrast is acquired. A difference image is calculated by superimposing upon and subtracting the mask image from the contrast image. Ideally, nothing appears in the difference image other than the image of the blood vessels. Because of the time difference between acquisition of the mask image (no contrast) and acquisition of the contrast-enhanced images, global and periodic motion, fluctuations in the intensity of the X-ray source, scattering by the contrast medium, etc., unwanted artifacts may appear in the differenced or digitally subtracted angiographic image.

DSA is useful in the diagnosis and imaging of various blood vessel disorders, such as arterial and venous occlusions, including carotid artery stenosis, pulmonary embolisms and acute limb ischemia; arterial stenosis, particularly for renal artery stenosis; and cerebral aneurysms and arteriovenous malformations.

SUMMARY OF THE INVENTION

The background art describes methods to perform DSA, which unfortunately suffer from a number of drawbacks and inefficiencies. As currently performed in the art and as described above, DSA requires the acquisition of a non-contrast initial or "mask" image, followed by sequential enhanced contrast images. Subtraction of each of the enhanced images from the non-enhanced image is performed and viewed by the doctor, enabling the blood vessels and any problems therewith to be easily seen. However, if any movement occurs between obtaining the non-enhanced image and the enhanced image, these images will not be in registration and so the subtraction process will not be performed correctly.

The present invention overcomes the above drawbacks of the background art by providing, in at least some embodiments, a system and method for efficiently performing DSA (digital subtraction angiography), which does not require a non-enhanced or "mask" image to be obtained. In fact, the method and system are operative without the mask image. Instead, a plurality of contrast enhanced images are obtained, such that at least two but preferably at least three images are obtained and more preferably 10 images are obtained (or even more). Next, optionally and preferably a registration is performed between these images, which may optionally be a rigid registration or a non-rigid registration, performed according to any suitable method. Optionally and preferably registration is performed by using a known registration method, non-limiting examples of which are described with regard to "Algorithms for radiological image registration and their clinical application" by Hawkes et al (J. Anat. (1998) 193, pp. 347-361); "Image registration: an essential tool for nuclear medicine" by Hutton et al (Eur J Nucl Med (2002) 29: pp 559-577); and US Patent Application No. 20100235352; all of which are hereby incorporated by reference as if fully set forth herein. Of course, other registration methods could also optionally be used in place of, or in addition to, the methods described in these papers.

Next, each image (or volume) is subtracted from the previous image (or volume) through subtracting the pixels. Volumes are subtracted for 3-dimensional images; however where reference is made to subtracting "images" it may also be understood to encompass subtracting "volumes". The process of subtracting the pixels may optionally comprise taking the absolute value after subtraction, or alternatively selecting the greater of the value after subtraction or a threshold value, wherein the threshold value is greater than or equal to zero. For example, the former operation may optionally be described as $R=|i\_2-i\_1|$, in which R is the absolute value after subtraction of the value of two pixels $i\_1$ and $i\_2$. The latter operation may optionally be described as $R=MAX(i\_2-i\_1, thresh)$, where thresh is some threshold value greater than or equal to zero; optionally alternatively, this calculation may be made through a dedicated lookup table that will be generated according to a known equation. Such a lookup table may optionally be used for any function and not only subtraction, in order to apply this function to the value of pairs of pixels. Next, tMIP (temporal maximum intensity projection) is optionally and preferably performed using several (1-N) result images, which are the images obtained after the above subtraction process.

Optionally, a cine view of the results may be provided, assuming that the tMIP is performed on images that have been divided into a plurality of non-zero sets, such that there exists at least two images after tMIP is performed. Also optionally and preferably, one or more noise reduction algorithm and smoothing algorithms are applied to improve the results, including but not limited to passing a median or Gaussian filter, another method is called anisotropic diffusion or Perona-Malik diffusion (see scale-space and edge detection using anisotropic diffusion by Perona and Malik, Pattern Analysis and Machine Intelligence, IEEE Transactions, July 1990, Volume: 12, Issue: 7, Page(s): 629-639). As noted below, optionally one or more noise reduction algorithm and smoothing algorithms are applied before subtraction of the pixels as described above, additionally or alternatively.

The term "image data" as used herein relates to two or three dimensional image data unless otherwise indicated.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

Although the present invention is described with regard to a "computer" on a "computer network", it should be noted that optionally any device featuring a data processor and the ability to execute one or more instructions may be described as a computer, including but not limited to any type of personal computer (PC), a server, a cellular telephone, an IP telephone, a smart phone, a PDA (personal digital assistant), or a pager. Any two or more of such devices in communication with each other may optionally comprise a "computer network".

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the drawings.

DESCRIPTION OF AT LEAST SOME EMBODIMENTS

At least some embodiments of the present invention are now described with regard to the following illustrations and accompanying description, which are not intended to be limiting in any way.

Figure 1:
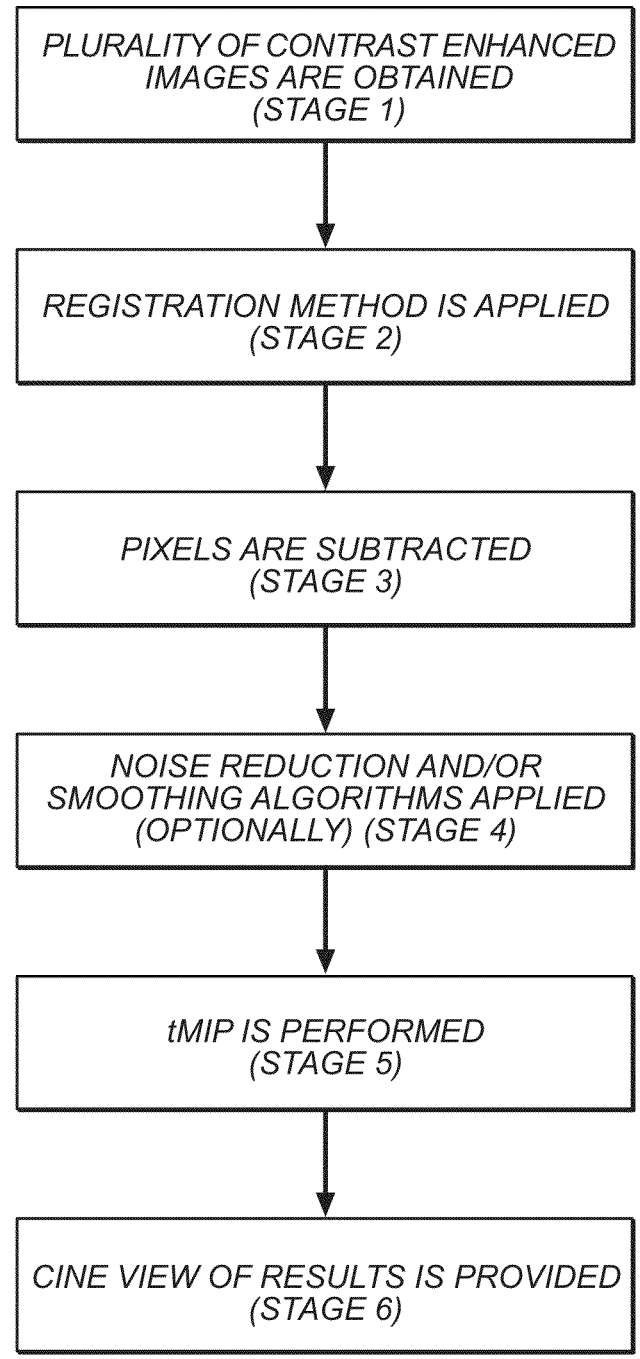
FIG. 1 shows an exemplary, illustrative method for efficiently performing DSA (digital subtraction angiography) according to at least some embodiments of the present invention.

Referring now to the drawings, FIG. 1 shows an exemplary, illustrative method for efficiently performing DSA (digital subtraction angiography) according to at least some embodiments of the present invention. In stage 1, a plurality of contrast enhanced images are obtained, such that at least two but preferably at least three images are obtained and more preferably 10 images are obtained (or even more). Next, in stage 2, optionally and preferably a registration is performed between these images, whether rigid or non-rigid. Optionally and preferably registration is performed by using a known registration method, non-limiting examples of which are described with regard to "Algorithms for radiological image registration and their clinical application" by Hawkes et al (J. Anat. (1998) 193, pp. 347-361); "Image registration: an essential tool for nuclear medicine" by Hutton et al (Eur J Nucl Med (2002) 29: pp 559-577); and US Patent Application No. 20100235352; all of which are hereby incorporated by reference as if fully set forth herein. Of course, other registration methods could also optionally be used in place of, or in addition to, the methods described in these papers.

In stage 3, optionally and preferably after registration, but alternatively and optionally without performing registration, each image is subtracted from the previous image through subtracting the pixels. It is to be noted that since the method is performed without obtaining a mask image, only the contrast-enhanced images are subtracted.

The process of subtracting the pixels may optionally comprise taking the absolute value after subtraction, or alternatively selecting the greater of the value after subtraction or a threshold value, wherein the threshold value is greater than or equal to zero. For example, the former operation may optionally be described as $R=|i\_2-i\_1|$, in which R is the absolute value after subtraction of the value of two pixels $i\_1$ and $i\_2$. The latter operation may optionally be described as $R=MAX(i\_2-i\_1, thresh)$, where thresh is some threshold value greater than or equal to zero; optionally alternatively, this calculation may be made through a dedicated lookup table that will be generated according to a known equation.

Also optionally and preferably, in stage 4, one or more noise reduction algorithm and smoothing algorithms are applied to improve the results, including but not limited to passing a median or Gaussian filter, while another method is called anisotropic diffusion or Perona-Malik diffusion (see scale-space and edge detection using anisotropic diffusion by Perona and Malik, Pattern Analysis and Machine Intelligence, IEEE Transactions, July 1990, Volume: 12, Issue: 7, Page(s): 629-639). Optionally one or more noise reduction algorithm and smoothing algorithms are applied after registration and/or after application of tMIP, additionally or alternatively.

In stage 5, tMIP (temporal maximum intensity projection) is done using several (1-10) result images. Maximum intensity projection (MIP) is a common and powerful tool for rendering three-dimensional volume image data sets, and is particularly useful in connection with magnetic resonance angiographic images. tMIP is the MIP process performed over the temporal axis, so that it is operative for either two-dimensional or three-dimensional data.

In stage 6, optionally, a cine view of the results may be provided, assuming that the tMIP is performed on images that have been divided into a plurality of non-zero sets, such that there exists at least two images after tMIP is performed. The number of images in each tMIP set is optionally determined as a parameter, for example through user input. For example, suppose that the subtraction stage, stage 3, resulted in images $i\_1 \ldots i\_N$. Also suppose that in stage 5 tMIP was performed on sets of 3 images each, resulting in the following process: $I\_1=tMIP(i\_1 \ldots i\_3)$, $I\_2=tMIP(i\_2 \ldots i\_4)$, etc. . . . until $I\_\{N-2\}$ images are formed in stage 5. Then stage 6 shows a cine view of $I\_1 \ldots I\_N-2$.

The above method is characterized in that it is performed without first obtaining a mask or non-contrast-enhanced image, yet is still able to successfully perform DSA. The method is preferably performed with tMIP to reduce image "jitter".

Figure 2A:
FIGS. 2A-2C shows some results after performing the method of FIG. 1, plus the original image.

FIG. 2A shows the resultant image after the method of FIG. 1 was performed, with tMIP of 4 images, but without the optional registration stage being performed.

Figure 2B:

FIG. 2B shows the resultant image after the method of FIG. 1 was performed, with tMIP of 6 images, but without the optional registration stage being performed.

Figure 2C:
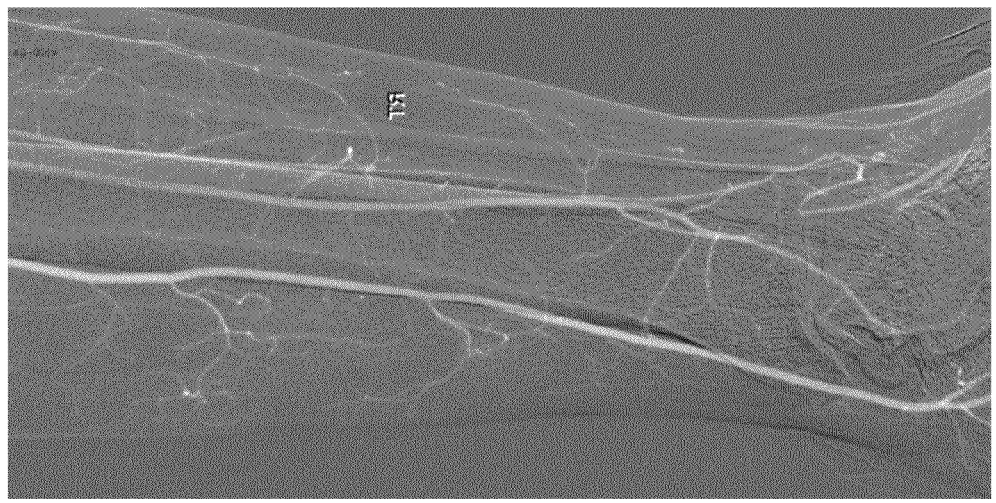

FIG. 2C shows the original DSA image with residual bone effects, created according to the regular DSA, but with subtraction by using a mask image.

Figure 3:
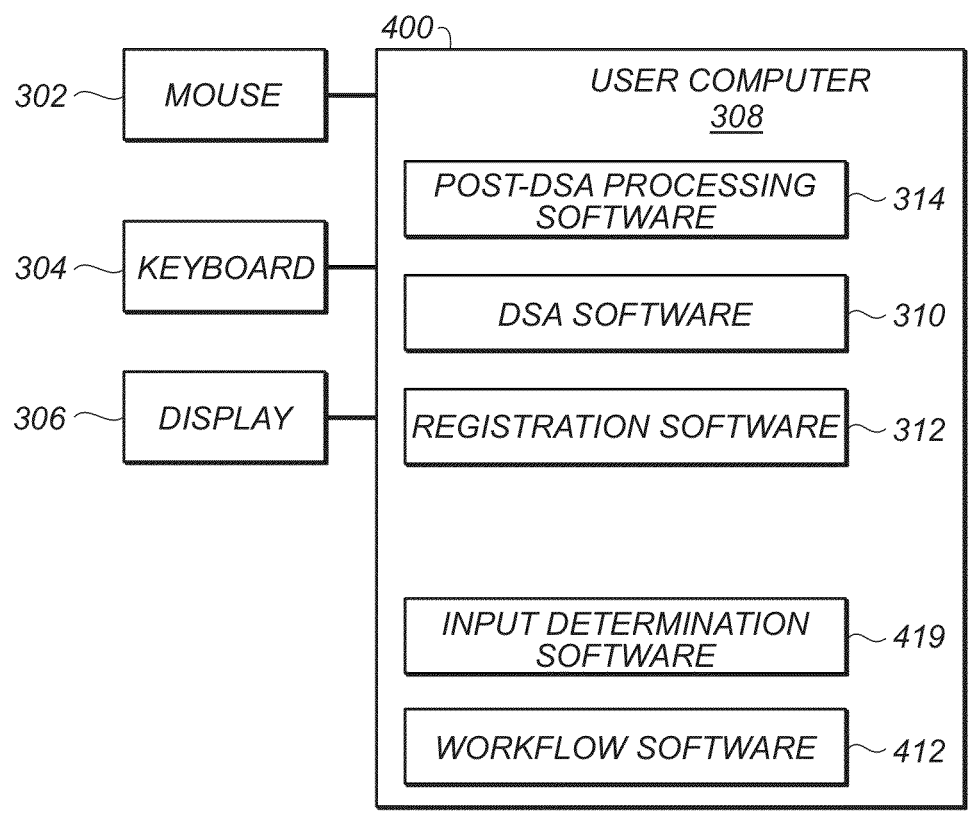
FIG. 3 shows an exemplary, non-limiting illustrative system according to at least some embodiments of the present invention.

FIG. 3 shows an exemplary, non-limiting illustrative system according to at least some embodiments of the present invention. As shown, a system 300 features a mouse 302 or other pointing device, a keyboard 304 and a display 306. Optionally any of these components may be combined, for example for a touch sensitive display screen; mouse 302 and keyboard 304 may optionally be described as an "input device". The user interacts with these components to perform the various methods as described herein where user interaction is indicated.

System 300 also features a user computer 308, which may optionally comprise any computational device and which may optionally be a local or remote computer, and may optionally be a plurality of computers. User computer 308 operates a DSA software 310 for performing DSA according to the method of FIG. 1, as described above.

System 300 additionally features a Registration software 312 for registering two sets of data, preferably through a global registration, for example optionally according to any suitable art known registration method. Registration is preferably performed before DSA, such that the image data is received by user computer 308 and is preferably first passed to registration software 312 before being processed by DSA software 310.

Optionally and preferably, after processing by DSA software 310, the image data undergoes tMIP and/or noise reduction and/or smoothing, by a post-DSA processing software 314. If tMIP is performed in addition to other operations, then preferably tMIP is performed first, before one or more other operations are performed.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method for efficiently performing DSA (digital subtraction angiography), comprising:
    obtaining a plurality of contrast enhanced images, wherein the plurality of contrast enhanced images do not include a mask image;
    performing a registration between the plurality of contrast enhanced images;
    subtracting each contrast enhanced image from the previous contrast enhanced image to form a plurality of result images; and
    performing tMIP (temporal maximum intensity projection) on the plurality of result images.

2. The method of claim 1, wherein the plurality of contrast enhanced images comprises at least 3 images.

3. The method of claim 2, wherein the plurality of contrast enhanced images comprises at least 10 images.

4. The method of claim 2, wherein the performing the registration comprises performing a rigid registration.

5. The method of claim 2, wherein the performing the registration comprises performing a non-rigid registration.

6. The method of claim 1, wherein the subtracting each contrast enhanced image comprises subtracting a value of pixels of each contrast enhanced image to form a subtraction product and taking an absolute value of the subtraction product.

7. The method of claim 1, wherein the subtracting each contrast enhanced image comprises subtracting a value of pixels of each contrast enhanced image to form a subtraction product and taking a greater of a threshold value or the subtraction product, wherein the threshold value is greater than or equal to zero.

8. The method of claim 1, further comprising performing one or more of a noise reduction algorithm or a smoothing algorithm on the plurality of result images.

9. The method of claim 1, wherein the subtracting each image further comprises performing one or more of a noise reduction algorithm or a smoothing algorithm on the images before the subtracting.

10. The method of claim 1, wherein the performing tMIP comprises dividing the plurality of result images into a plurality of sets and performing tMIP on each set; the method further comprising providing a cine view of images after the performing the tMIP on the sets.

11. The method of claim 10, wherein the dividing the plurality of result images comprises determining a number of result images in each set.

12. The method of claim 1, wherein the subtracting each contrast enhanced image comprises subtracting a value of pixels of each contrast enhanced image to form a subtraction product and taking a greater of a threshold value or the subtraction product, wherein the threshold value is determined according to a lookup table.

13. The method of claim 1, wherein the subtracting each contrast enhanced image comprises subtracting a volume corresponding to each contrast enhanced image.

14. A method for efficiently performing DSA (digital subtraction angiography), consisting essentially of obtaining a plurality of contrast enhanced images, wherein the contrast enhanced images do not include a mask image; performing a registration between the plurality of contrast enhanced images; subtracting each contrast enhanced image from the previous contrast enhanced image to form a plurality of result images; and performing tMIP (temporal maximum intensity projection) on the plurality of result images.

15. A method for efficiently performing DSA (digital subtraction angiography), comprising:
    obtaining a plurality of images, wherein the plurality of images consist essentially of contrast enhanced images, wherein the plurality of images does not include a mask image;
    performing a registration between the plurality of contrast enhanced images;

subtracting each contrast enhanced image from the previous contrast enhanced image to form a plurality of result images; and performing tMIP (temporal maximum intensity projection) on the plurality of result images.

16. A method for efficiently performing DSA (digital subtraction angiography), consisting essentially of obtaining a plurality of contrast enhanced images, wherein the images do not include a mask image; performing a registration between the plurality of contrast enhanced images; subtracting each contrast enhanced image from the previous contrast enhanced image to form a plurality of result images; dividing the plurality of result images into a plurality of sets; performing tMIP (temporal maximum intensity projection) on each set to form post-tMIP images; and providing a cine view of the post-tMIP images.

17. A method for efficiently performing DSA (digital subtraction angiography), consisting essentially of obtaining a plurality of contrast enhanced images, wherein the images do not include a mask image; performing registration between the plurality of contrast enhanced images; performing one or more of a noise reduction algorithm or a smoothing algorithm on the contrast enhanced images; subtracting each contrast enhanced image from the previous contrast enhanced image to form a plurality of result images; dividing the plurality of result images into a plurality of sets; performing tMIP (temporal maximum intensity projection) on each set to form post-tMIP images; and providing a cine view of the post-tMIP images.

18. A method for efficiently performing DSA (digital subtraction angiography), consisting essentially of obtaining a plurality of contrast enhanced images, wherein the images do not include a mask image; performing a registration between the plurality of contrast enhanced images; subtracting each contrast enhanced image from the previous contrast enhanced image to form a plurality of result images; performing one or more of a noise reduction algorithm or a smoothing algorithm on the contrast enhanced images; dividing the plurality of result images into a plurality of sets; performing tMIP (temporal maximum intensity projection) on each set to form post-tMIP images; and providing a cine view of the post-tMIP images.

19. The method of claim 1, wherein the step of performing comprises:

performing tMIP on the plurality of result images results to generate at a plurality of tMIP result images; and displaying, storing, or transmitting at least one of the plurality of tMIP result images.

\* \* \* \* \*